US006782351B2

(12) United States Patent
Reichel et al.

(10) Patent No.: US 6,782,351 B2
(45) Date of Patent: Aug. 24, 2004

(54) AIR QUALITY MONITORING AND SPACE MANAGEMENT SYSTEM COUPLED TO A PRIVATE COMMUNICATIONS NETWORK

(75) Inventors: Bryan S. Reichel, Credit River Township, MN (US); Joseph L. Wolf, Shakopee, MN (US)

(73) Assignee: PureChoice, Inc., Lakeville, MN (US)

( * ) Notice: Subject to any disclaimer, the term of this patent is extended or adjusted under 35 U.S.C. 154(b) by 112 days.

(21) Appl. No.: 10/138,111

(22) Filed: May 1, 2002

(65) Prior Publication Data
US 2003/0051023 A1 Mar. 13, 2003

Related U.S. Application Data
(60) Provisional application No. 60/322,107, filed on Sep. 11, 2001.

(51) Int. Cl.[7] .......................... G06F 19/00; G08B 23/00
(52) U.S. Cl. .................. 702/188; 702/104; 340/870.16; 340/501
(58) Field of Search .......................... 702/188, 85, 104, 702/22, 23, 24, 26, 30, 31, 32; 340/870.04, 870.16, 501; 73/31.01, 31.02, 31.03

(56) References Cited

U.S. PATENT DOCUMENTS

| | | | |
|---|---|---|---|
| 4,019,677 A | 4/1977 | Dotschkal et al. | |
| 4,026,263 A | 5/1977 | Boyd | |
| 4,049,196 A | 9/1977 | Bergami, Jr. et al. | |
| 4,374,515 A | 2/1983 | Conrad | |
| 4,389,620 A | 6/1983 | Yamaguchi | |
| 4,706,553 A | 11/1987 | Sharp et al. | |
| 4,773,311 A | 9/1988 | Sharp | |
| 4,823,290 A | 4/1989 | Fasack et al. | |
| 4,893,551 A | 1/1990 | Sharp et al. | |
| 5,001,463 A | 3/1991 | Hamburger | |
| 5,017,989 A | 5/1991 | Street et al. | |
| 4,706,553 A | 7/1993 | Sharp et al. | |
| 5,240,455 A | 8/1993 | Sharp | |
| 5,251,665 A | 10/1993 | Schaufeld | |
| 5,255,556 A | 10/1993 | Lobdell | |
| 5,304,093 A | 4/1994 | Sharp et al. | |
| 5,311,451 A | 5/1994 | Barrett | |
| 5,356,594 A | 10/1994 | Neel et al. | |
| 5,385,505 A | 1/1995 | Sharp et al. | |
| 5,400,246 A | 3/1995 | Wilson et al. | |
| 5,406,073 A | 4/1995 | Sharp et al. | |

(List continued on next page.)

FOREIGN PATENT DOCUMENTS

FR    2556820    6/1985

OTHER PUBLICATIONS

"MPM–4100 IA1 ColoPpac: Indoor Air Quality Measurement System", by Solomat, A NEOTRONICS Company (4 pages), 1994.
Kishkovich et al., "Immediate Results Offer Advantages—Real–Time Monitoring For Low–Level Pollution", ASHRAE Journal, Nov. 1997, pp. 46–51.

*Primary Examiner*—Patrick Assouad
(74) *Attorney, Agent, or Firm*—Faegre & Benson LLP

(57) ABSTRACT

An air quality monitoring system at a site having a private communications network adapted to carry data traffic. The air quality monitoring system includes at least one sensor assembly programmed to collect air quality data at the site. The sensor assembly includes at least one air quality sensor adapted to measure a level of an air quality attribute. The air quality sensor is coupled to a microprocessor and a data storage device. A communications device couples the microprocessor to the private communications network. A public communications network is coupled to the private communications network. An archiving and processing system at a remote data collection site is coupled to the public communications network. The archiving and processing system includes a controller programmed to automatically store air quality data in the database from one or more sensor assemblies.

100 Claims, 3 Drawing Sheets

U.S. PATENT DOCUMENTS

| | | | | |
|---|---|---|---|---|
| 5,435,779 A | | 7/1995 | Sharp et al. | |
| 5,491,473 A | | 2/1996 | Gilbert | |
| 5,491,789 A | | 2/1996 | Aramaki et al. | |
| 5,520,328 A | | 5/1996 | Bujak, Jr. | |
| 5,545,086 A | | 8/1996 | Sharp et al. | |
| 5,553,006 A | * | 9/1996 | Benda | 700/276 |
| 5,568,385 A | | 10/1996 | Shelton | |
| 5,617,337 A | | 4/1997 | Eidler et al. | |
| 5,687,098 A | | 11/1997 | Grumstrup et al. | |
| 5,798,945 A | | 8/1998 | Benda | |
| 5,802,285 A | | 9/1998 | Hirviniemi | |
| 5,831,848 A | | 11/1998 | Rielly et al. | |
| 5,831,876 A | | 11/1998 | Orr et al. | |
| 5,892,690 A | * | 4/1999 | Boatman et al. | 700/276 |
| 5,938,823 A | | 8/1999 | Condit et al. | |
| 5,944,823 A | | 8/1999 | Jade et al. | |
| 5,963,146 A | | 10/1999 | Johnson et al. | |
| 5,971,067 A | | 10/1999 | Rayburn et al. | |
| 5,978,373 A | | 11/1999 | Hoff et al. | |
| 5,983,890 A | | 11/1999 | Thomas et al. | |
| 5,999,973 A | | 12/1999 | Glitho et al. | |
| 6,122,281 A | | 9/2000 | Donovan et al. | |
| 6,125,710 A | * | 10/2000 | Sharp | 73/863.31 |
| 6,137,403 A | | 10/2000 | Desrochers et al. | |
| 6,157,950 A | | 12/2000 | Krishnan | |
| 6,172,616 B1 | | 1/2001 | Johnson et al. | |
| 6,181,681 B1 | | 1/2001 | Hiscock et al. | |
| 6,188,691 B1 | | 2/2001 | Barkai et al. | |
| 6,205,490 B1 | | 3/2001 | Karapetkov et al. | |
| 6,215,789 B1 | | 4/2001 | Keenan et al. | |
| 6,216,956 B1 | * | 4/2001 | Ehlers et al. | 236/47 |
| 6,252,689 B1 | | 6/2001 | Sharp | |
| 6,358,374 B1 | | 3/2002 | Obee et al. | |
| 6,425,297 B1 | * | 7/2002 | Sharp | 73/863.33 |
| 6,466,133 B1 | * | 10/2002 | Skardon | 340/627 |
| 6,487,457 B1 | * | 11/2002 | Hull et al. | 700/17 |
| 2002/0144537 A1 | * | 10/2002 | Sharp et al. | 73/31.01 |
| 2002/0152298 A1 | * | 10/2002 | Kikta | 709/223 |

* cited by examiner

AIR QUALITY MONITORING AND SPACE MANAGEMENT SYSTEM COUPLED TO A PRIVATE COMMUNICATIONS NETWORK

This application claims the benefit of U.S. Provisional Application serial No. 60/322,107 filed Sep. 11, 2001.

FIELD OF THE INVENTION

The present invention relates to an air quality monitoring and space and energy management system that uses the infrastructure of a private communications network, and to an air quality sensor for the system.

BACKGROUND OF THE INVENTION

The typical approach to providing satisfactory air quality in work spaces or living spaces is to measure contaminant concentrations in the space, both in terms of gas or vapor concentrations (i.e., CO, $CO_2$ or other noxious gases), or airborne particulate concentrations. The measured values are then compared with safe or recommended air quality conditions. Measurement of air quality, however, typically requires complex and expensive equipment to be used by specially trained personnel.

SUMMARY OF THE INVENTION

The present invention relates to an air quality monitoring and space management system that sends air quality data over the existing private communications network, such as a local area network, at a site. In one embodiment, the air quality data can be uploaded to a second private communications network via a public communications network. The second private communications network provides archiving and data processing functions, such as trend analysis. The second private communications network can also send alerts when an air quality attribute exceeds a predetermined value. Alerts can also be sent if the trend of an air quality attribute is predicted to exceed a predetermined value during a predetermined time sequence. Remote access to the air quality data is provided through the public communications network.

The present air quality monitoring system works in conjunction with a private communications network adapted to carry data traffic at a site. The air quality monitoring system includes at least one sensor assembly programmed to collect air quality data at the site. The sensor assembly includes at least one air quality sensor adapted to measure a level of an air quality attribute. The air quality sensor is coupled to a microprocessor and a data storage device. A communications device couples the microprocessor to the private communications network. A public communications network is coupled to the private communications network. An archiving and processing system at a remote data collection site comprises a controller programmed to automatically acquire over the public communications network air quality data from one or more sensor assemblies and to automatically store air quality data in a database.

The air quality sensors are typically adapted to measure different air quality attributes. Each sensor assembly preferably comprises a sensor assembly identification number. In one embodiment, the air quality data for a particular sensor comprises a format specific to the air quality attribute being measured. The air quality data for a particular site can be associated with a site identification number.

The air quality sensors typically output a voltage signal proportional to a measured level of an air quality attribute.

The microprocessor is programmed to convert sensor data to air quality data. In one embodiment, the microprocessor is programmed to convert sensor data to an industrial control protocol. In another embodiment, the microprocessor is programmed to convert sensor data to an industrial control protocol compatible with HVAC equipment. The microprocessor can be coupled to an HVAC controller directly or through the private communications network.

The microprocessor can be programmed to systematically collect air quality data from the air quality sensors at defined intervals and to transmit the air quality data to the private communications network. The microprocessor can also be programmed to systematically collect air quality data from the air quality sensors at defined intervals and to transmit the air quality data over the private communications network and the public communications network to the archiving and processing system. The microprocessor can also be programmed to systematically collect air quality data from the air quality sensors at defined intervals and to store the air quality data in the data storage device. The archiving and processing system is typically a second private communications network coupled to the public communications network.

The data storage device is preferably a read/write semiconductor memory device. The data storage device preferably has sufficient storage capacity to store air quality data for a period of time (e.g., one week). The data storage device can optionally include an error correction table for one or more of the air quality sensors. In one embodiment, the data storage device includes a calibration table for one or more of the air quality sensors. The microprocessor can optionally be programmed to adjust sensor data from a first sensor in response to sensor data collected by a second sensor. In another embodiment, the microprocessor is programmed to modify an error correction table for a first sensor in response to sensor data from a second sensor.

In one embodiment, a heater sensing and control circuit is coupled to the microprocessor. A heater controlled by the heater sensing and control circuit is operatively coupled to one or more temperature dependent sensors. The microprocessor is preferably programmed to calibrate one or more of the temperature dependent sensors. In another embodiment, the microprocessor is programmed to control and adjust one or more heaters adjacent to one or more temperature dependent sensors to maintain an operating temperature within a specified tolerance. In yet another embodiment, the microprocessor is adapted to combine air quality data from two or more air quality sensors to provide an air quality index. Alternatively, the archiving and processing system is adapted to combine air quality data from two or more air quality sensors to provide an air quality index. In another embodiment, the sensor is adapted to provide a relative indication of air quality based upon the presence of a plurality of VOC's.

In one embodiment, the communications device comprises a semiconductor communications driver. The communications device is preferably programmed to transmit digital data corresponding to the air quality data to the private communications network. In another embodiment, the microprocessor is programmed to convert the sensor data into a protocol compatible with the communications interface and/or the private communications network.

The present system includes remote sites coupled to the database through the public communications network.

In one embodiment, the archiving and processing system is programmed to send an alert signal when air quality data is outside defined operating parameters. The alert signal can be sent over the public communications network to one of the private communications networks or a remote site. The alert signal can be one or more of an e-mail message, an automated telephone message, an automated fax, or an automated pager message.

In another embodiment, the controller is programmed to calculate trends in air quality data. The archiving and processing system is programmed to send an alert signal when a calculated trend predicts that air quality data will be outside defined operating parameters within a defined time interval.

The present invention is also directed to a method for monitoring air quality comprising the steps of coupling one or more sensor assemblies programmed to collect air quality data to a private communications network located at a site. The level of one or more air quality attributes is measured using air quality sensors in the sensor assemblies. The sensor data is converted to air quality data. The air quality data is uploaded to the private communications network. The air quality data is transmitted over a public communications network to a second private communications network. The air quality data from one or more sensor assemblies is automatically stored in a database on the second private communications network. Access to the air quality data in the database is provided through the public communications network.

The present invention is also directed to a sensor assembly for use at a site having a private communications network that is adapted to carry data traffic. The sensor assembly includes at least one air quality sensor adapted to measure a level of an air quality attribute. A microprocessor is coupled to the air quality sensor and to a data storage device. The microprocessor is programmed to convert sensor data to a protocol compatible with the private communications network. A communications device couples the microprocessor to the private communications network.

The present invention is also directed to a sensor assembly for use at a site having an HVAC controller that is adapted to control HVAC equipment in response to environmental conditions. The sensor assembly includes at least a first air quality sensor and a second air quality sensor each adapted to measure a level of at least one air quality attribute. A microprocessor is coupled to the air quality sensors and to a data storage device. The microprocessor is programmed to convert sensor data to a protocol compatible with the HVAC controller. The microprocessor is also programmed to adjust sensor data from the first air quality sensor in response to sensor data collected by the second air quality sensor. A communications device couples the microprocessor to the HVAC controller.

In various embodiments, the microprocessor can be programmed to modify an error correction table or run an error correction algorithm for the first air quality sensor in response to sensor data from the second air quality sensor. In another embodiment, the air quality data from the first air quality sensor is modified in response to temperature data above or below a temperature threshold. In yet another embodiment, the microprocessor is coupled to the HVAC controller through a private communications network.

DETAILED DESCRIPTION OF THE PREFERRED EMBODIMENTS

Figure 1:
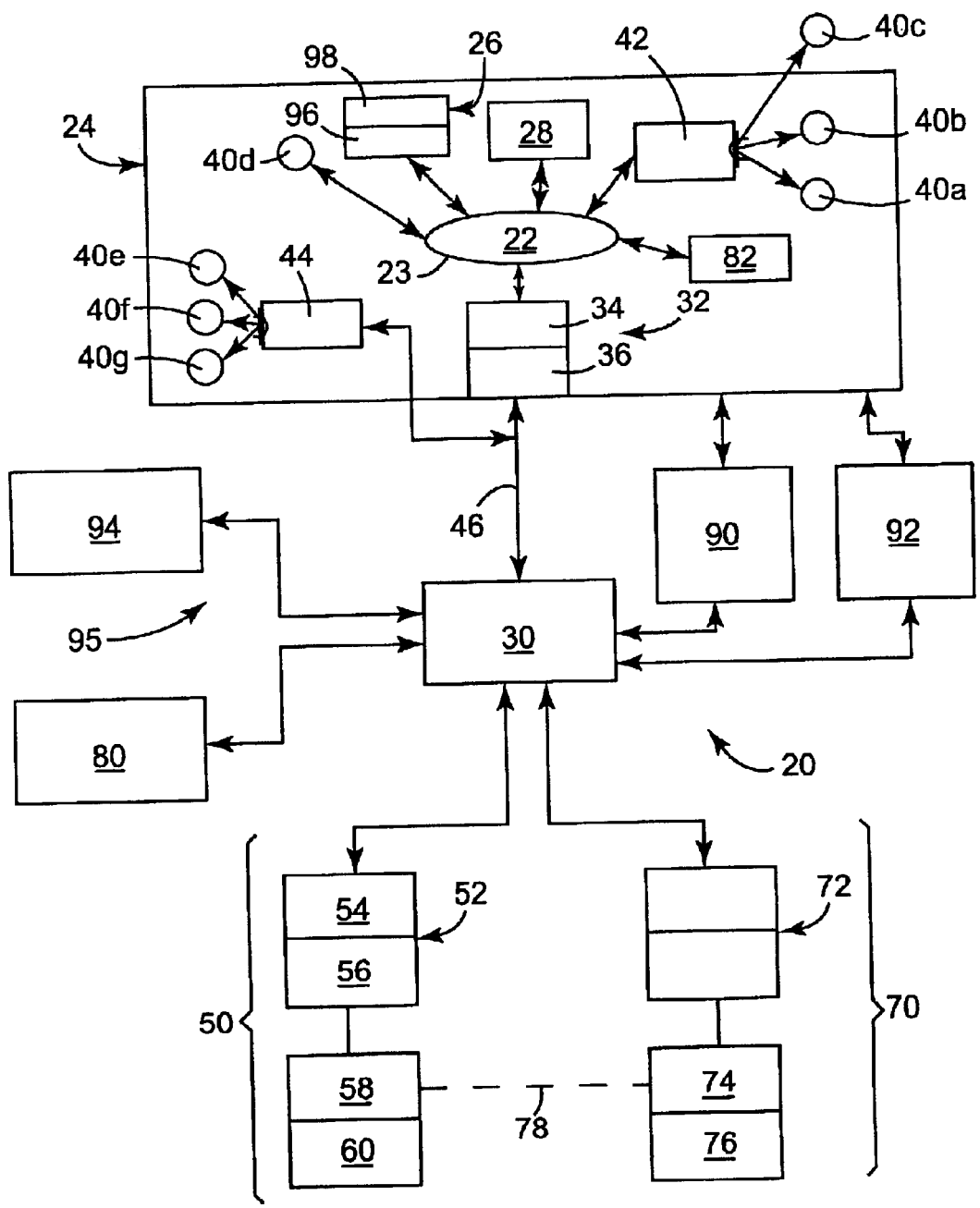
FIG. 1 is a schematic illustration of an air quality monitoring system and a space management system coupled to a private communications network.

FIG. 1 is a schematic illustration of an air quality monitoring system 20 coupled to a private communications network 22 at site 24 in accordance with the present invention. The private communications system 22 includes network infrastructure 23, such as wiring and access ports (e.g., RJ-45, RJ-14, RJ-11, and fiber optic jacks), located around the site 24. In another embodiment, the access ports are connected to the private communications network 22 by RF communications devices. The private communications network 22 can be a local area network (LAN) (e.g., as an Ethernet LAN or a token ring LAN), an Intranet, an Extranet, or a Virtual Private Network (VPN). In the illustrated embodiment, private communications network 22 is a LAN with computer workstations 26, 28. As used herein, "private communications system" refers to a network, such as a local area network, an Intranet, an Extranet, a Virtual Private Network or any other communication structure designed to carry data between a plurality of computers located at a site. The private communications system is typically digital, but may contain one or more analog segments, such as a modem, in the various communications channels.

A local area network (LAN) is a group of computers (or associated devices such as servers, printers, disk drives, routers, etc.) that share a common digital communications line and typically share the resources of one or more processors or server within a small geographic area (for example, within an office building). The server can have applications and data storage that are shared in common by multiple computer users. A local area network may serve as few as two or three users (for example, in a home network) or many as thousands of users (for example, in an FDDI network).

An Intranet is a private network that is contained within an organization. It may consist of many interlinked local area networks and also uses leased lines in a wide area network or the Internet. An Intranet uses TCP/IP, Hypertext Transfer Protocol, and other Internet protocols and in general looks like a private version of the Internet. With tunneling, companies can send private messages through the public communications network, using the public communications network with special encryption/decryption and other security safeguards to connect one part of their Intranet to another. The "tunnel" is the particular path that a given company message or file might travel through the Internet. A protocol or set of communication rules called Point-to-Point Tunneling Protocol (PPTP) makes it possible to create a virtual private network (VPN) through "tunnels" over the Internet, providing secure wide-area communications using public communications networks. When a portion of an Intranet is made accessible to customers, partners, suppliers, or others outside the company, that portion of the Intranet becomes part of an Extranet.

A virtual private network (VPN) is a private data network that makes use of the public telecommunication infrastructure, maintaining privacy through the use of a tunneling protocol and security procedures. A virtual private network can be contrasted with a system of owned or leased lines that can only be used by one company. The idea of the VPN is to give the company the same capabilities at much lower cost by using the shared public infrastructure rather than a private one. A virtual private network makes it possible to have the same secure sharing of public resources for data. Using a virtual private network involves encrypting data before sending it through the public communications network and decrypting it at the receiving end. An additional level of security involves encrypting not only the data but also the originating and receiving network addresses. Various embodiments of private communications systems suitable for use in the present invention are disclosed in U.S. Pat. No. 5,802,285 (Hirviniemi); U.S. Pat. No. 5,978,373 (Hoff et al.); U.S. Pat. No. 6,157,950 (Krishnan); U.S. Pat. No. 6,188,691 (Barkai et al.); and U.S. Pat. No. 6,215,789 (Keenan et al.).

The private communications network 22 communicates with public communications network 30 through gateway 32 and communications channel 46. The gateway 32 typically includes a web server 34 and a proxy server 36. The proxy server 36 is a server that acts as an intermediary between the private communications network 22 and the public communications network 30 so that the site 24 can ensure security and administrative control.

In some embodiments, the proxy server 36 is associated with or part of firewall server that protects the private communications network 22 from outside intrusion. A firewall is a set of related programs, located at the gateway 32 that protects the resources of a private communications network 22 from users from other networks. Where private communications network 22 is an Intranet, a firewall prevents unauthorized users from accessing the network 22 and controls what outside resources users of the private communications network 22 have access to. Basically, a firewall, working closely with a router program, examines each network packet to determine whether to forward it toward its destination. A firewall also includes or works with a proxy server that makes network requests on behalf of workstation users. A firewall is often installed in a specially designated computer separate from the rest of the network so that no incoming request can get directly at private network resources. Various techniques for passing data between a private communications network and a public communications network are disclosed in U.S. Pat. No. 5,944,823 (Jade et al.); U.S. Pat. No. 5,963,146 (Johnson et al.); U.S. Pat. No. 5,999,973 (Glitho et al.); U.S. Pat. No. 6,122,281 (Donovan et al.); U.S. Pat. No. 6,181,681 (Hiscock et al.); U.S. Pat. No. 6,172,616 (Johnson et al.); and U.S. Pat. No. 6,205,490 (Karapetkov et al.).

The public communications network 30 can be a wide area network, an Extranet or the Internet. The Internet, sometimes called simply "the Net," is a worldwide system of computer networks—a network of networks in which users at any one computer can, if they have permission, get information from any other computer (and sometimes talk directly to users at other computers). Physically, the Internet uses a portion of the total resources of the currently existing public telecommunication networks. Technically, what distinguishes the Internet is its use of a set of protocols called TCP/IP (Transmission Control Protocol/Internet Protocol). Intranets and Extranets also make use of the TCP/IP protocol.

A wide area network (WAN) is a geographically dispersed telecommunications network and the term distinguishes a broader telecommunication structure from a local area network. A wide area network may be privately owned or rented, but the term usually connotes the inclusion of public (shared user) networks. The WAN may be any connection, such as a telephone line, X.25 line, lease line, asynchronous link, SNA network, integrated services digital network (ISDN), and the like.

A plurality of sensor assemblies 40a, 40b, 40c, 40d, 40e, 40f, 40g (collectively referred to herein as "40") are coupled to the network infrastructure 23 of the private communications network 22. In one embodiment, one or more sensor assemblies 40 are coupled directly to an access ports (e.g., RJ-45, RJ-14 and RJ-11 jacks) on the site 24, such as for example the sensor assembly 40d that is compatible with Ethernet protocol. Consequently, the sensor assemblies 40 can typically be located throughout the site 22 without the need for additional wiring. As used herein, "coupled" refers to an interconnection that permits data to be exchanged between two or more device.

The sensor assemblies 40 preferably permit seamless device plug-in. This feature gives users the ability to plug the sensor assembly 40 into the private communications network 20 and have the network 20 recognize that the sensor assembly is there and applies the appropriate drivers. The user doesn't have to tell the network 20.

The sensor assemblies 40 are preferably positioned at various distributed locations in a particular site 24. The number and arrangement of the sensor assemblies 40 shown in FIG. 1 is for illustrative purposes only and can vary depending upon the air quality monitoring requirements. As will be discussed below, each of the sensor assemblies 40 includes one or more sensors adapted to measure a level of an air quality attribute (see e.g., FIG. 2). As used herein, "air quality attribute" refers to a characteristic of the ambient air including without limitation temperature, humidity, pressure, the level of a particular gas or particulate, such as mold, toxins, VOC's, dust, and the like.

The sensor assemblies 40 can be coupled to the private communications network 22 using a variety of configurations. In one embodiment, the sensor assemblies 40a, 40b, 40c are coupled to a communications interface 42, which is coupled to the private communications network 22. The communications interface 42 converts sensor data from the sensor assemblies 40a, 40b, 40c into a protocol compatible with the private communications network 22. For example, the communications interface 42 can convert sensor data into an Internet protocol.

In another embodiment, the sensor data is converted to a first protocol at the sensor assembly 40 and the communications interface 42 converts the first protocol to a second protocol compatible with the private communications network 22. For example, the sensor data is converted at the sensor assemblies 40a, 40b, and 40c to an industrial control language sold under the trade name Lontalk™ available from Echelon Corp. Lontalk is a desirable format for the air quality data because of its compatibility with many heating, ventilating and air conditioning systems (HVAC). The communications interface 42, in turn, converts the air quality data to a format compatible with the private communications network 22, such as Internet protocol In the illustrated embodiment, sensor assembly 40c is located outside of the physical confines of the site 24. For example, the sensor assembly 40c can be located outside of the building defining the site 24 to measure air quality attributes that may affect air quality within the site 24. Sensor assembly 40c is useful to measure the migration of air quality attributes into and out of the site 24. Positioning one or more sensor assemblies outside of the site 24 is also useful for predicting trends in air quality attributes within the site 24.

In another embodiment, the communications interface 42 can be provided with each sensor assembly 40 so that the sensor assembly 40 can be coupled directly to the private communications network 22, such as sensor assembly 40d is connected directly to the private communications network 22. In this embodiment, microprocessor 102 (see FIG. 2) converts the sensor data to a format compatible with the private communications network 22, such as Ethernet protocol. In another embodiment, the sensor assemblies 40e, 40f, 40g are connected to a communications interface 44 that is coupled to the portion of the communications channel 46 located at the site 24 downstream of proxy server 36. This embodiment provides additional security for the private communications network 22.

The site 24 is preferably assigned a unique site identification number. Each sensor assembly 40 is preferably assigned an unique sensor assembly identification number. In one embodiment, each sensor within a sensor assembly 40 generates sensor data with a structure that is unique to that sensor. For example, temperature data is in a different format that humidity data. The combination of sensor assembly identification number and the data format is sufficient to uniquely identify which individual sensor is providing the data. In another embodiment, the microprocessor 102 can assign an unique sensor identification number to the data stream generated by each sensor within the sensor assembly 40. In any of these embodiments, the air quality data can be correlated to a particular air quality attribute measured by a sensor assembly 40 at the site 24.

Air quality data is uploaded from the sensor assemblies 40 to the private communications network 22 and subsequently through the public communications network 30 to a second private communications network 50. The second private communications network 50 is also referred to as the archiving and processing system. The second private communications network 50 includes a gateway 52, typically with a proxy server 54 and a web server 56 connected to a controller 58 that processes air quality data and maintains database 60. The second private communications network 50 is preferably located remotely from the site 24 to provide secure archiving. The second private communications network 50 also provides secure access to the air quality data through the public communications network 30 for both users at the site 24 and users at remote sites 80, 94.

A third private communications network 70 may optionally be used for redundancy. The third private communications network 70 also includes a gateway 72 and a controller 74 that maintains database 76. The third private communications network 70 is preferably located at a site physically remote from both the site 24 and the second private communications network 50. A synchronization connection 78 is optionally provided to synchronize the databases 60, 76.

Air quality data collected at site 24 can be upload through public communications network 30 to one or more private communications networks 50, 70 either continuously or at discrete time intervals. For example, if communications channel 46 is a dedicated communications line, a continuous stream of air quality data can be sent to the database 60 and/or 76. A dedicated line is a telecommunications path between two points that is available 24 hours a day for use by a designated user (individual or company). It is not shared in common among multiple users as dial-up lines are. A dedicated line can be a physical path owned by the user or rented from a telephone company, in which case it is called a leased line. A synonym is nonswitched line (as opposed to a switched or dial-up line).

In another embodiment, air quality data is uploaded to the private communications network 50 and/or 70 at discrete time intervals, such as every 10 or 20 seconds, whether or not the channel 46 is a dedicated line. Air quality data is optionally accompanied by the sensor assembly identification number, a site identification number and a time/data stamp when the air quality data was collected.

The controllers 58, 74 organize the air quality data to provide a comprehensive picture of the air quality attributes for the site 24. The controller 58 stores the air quality data in the database 60 using a variety of techniques. In one embodiment, air quality data is added to the database as a rolling average over a particular time interval (e.g., five minutes).

Data can be retrieved by the data collection program and dedicated computer at a regular interval, adjustable by editing the "time interval" field in a database that controls operation of the collection computer. Discrete "snapshot" values can be averaged together to compute an average value for all five parameters monitored. The master database is preferably updated periodically as soon as a new average has been computed, typically within a few seconds of having retrieved the data, such as for example via the Internet.

Customers can access the data through an Internet connection and see trend charts of average, hourly or daily values extending back in time over predetermined intervals. Customers can also view the instantaneous (updated once every 20 seconds in this example) data value for each sensor assembly through another custom designed interface called the real-time viewer. In one embodiment, records of five-minute averages for all sites and sensors are retained indefinitely.

Historical data going back a year or more is preferably available to the customer through the Internet interface at any time. To manage data access more effectively and speed up customer access to the data records, historical data are maintained in two separate databases: one containing all data for the last month, a second for all data older than 32 days. A custom-built software program and sensing logic automatically and transparently routes a customer request for data older than 32 days to the second database. Most often the typical customer is interested in recent data. Thereby the processing power of the web server can be devoted to the much smaller database of 32 days for the majority of customer transactions. This allows maximum processing speed and minimum access time.

If any of the air quality data exceeds predetermined thresholds, an automatic alert can be sent using a variety of techniques. In one embodiment, an automatic e-mail is sent from the private communications network 50 over the public communications network 30 to a remote user 80 and/or to any user in the private communications network 22. In another embodiment, the controller 58 can initiate an automated call to a telephone or a pager through the public communications network 30. In yet another embodiment, an alert signal is sent by the controller 58 through the public communications network 30 to a alert device 82 connected to the private communications network 22 at the site 24.

In an alternate embodiment, air quality data collected by the sensor assemblies 40 is stored and/or processed on the private communications network 22 at the site 24. For example, the workstation 26 can include a controller 96 and database 98. The workstation 26 can process the air quality data and maintain the database 98 substantially as done at the second private communications site 50. The database 98 can be accessed through the private communications network 22, such as from workstation 28 and/or at a remote site 80 through the public communications network 30.

In another alternate embodiment, air quality data collected by the sensor assemblies 40 is stored on both the private communications network 22, such as on workstation 26 and on the second private communications network 50. The redundancy provided by the databases 60 and 98 may obviate the third private communications network 70.

The site 24 is connected to various utility providers 90, 92 such as electric, natural gas, telecommunications, security, and the like. In another embodiment, the cost of the present air quality monitoring system 20 is billed to the site 24 along with the utility services. This embodiment takes advantage of the billing infrastructure of the utility providers 90, 92.

Thus, as described, the air quality monitoring system 20 of the present invention assures that air quality is automatically and systematically monitored without reliance upon schedules or priorities of personnel or individuals at the site 24. The air quality data collected by the sensor assemblies 40 is analyzed to control air quality or may be used for maintaining air quality records. For example, the data may be used to determine the frequency at which filtering devices, which are used to filter residues from the air, need to be changed.

Figure 2:
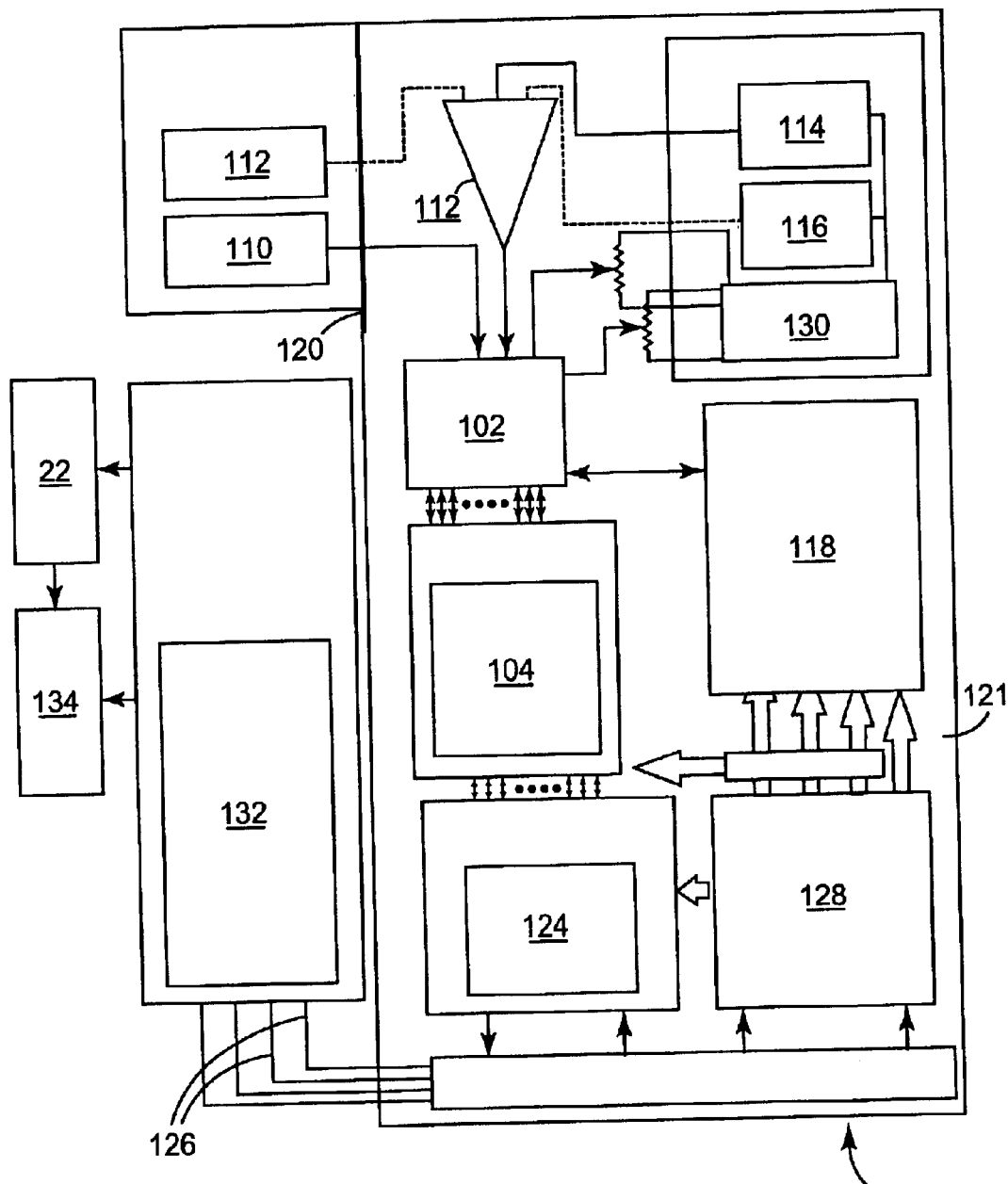
FIG. 2 is a schematic illustration of a sensor assembly in accordance with the present invention.

FIG. 2 is a schematic illustration of a sensor assembly 100 in accordance with the present invention. The sensor assembly 100 includes a microprocessor 102 operatively coupled to a memory storage device 104, such as a read/write semiconductor device. The storage device 104 preferably has sufficient capacity to store security protocols, to accept upgrades to the operating software, to maintain calibration data for the various sensors, and to maintain software for converting sensor data to a form usable by either the communications interface 42 or the private communications network 22. The memory storage device 104 can optionally have sufficient capacity to retain sensor data and/or air quality data for some period of time.

In the illustrated embodiment, the sensor assembly 100 includes a variety of sensors, such as digital thermometer 110, analog humidity sensor 112, analog odor and gases sensor 114 (e.g., VOC), analog CO sensor 116 and digital $CO_2$ sensor 118. The temperature sensor 110 and the humidity sensor 112 are preferably isolated from the other sensors by thermal barrier 120. The sensors 110, 112, 114, 116, 118 preferably continuously measure levels of the target air quality attribute, not just thresholds. Consequently, trends in air quality data can be tracked, as is discussed below. The entire sensor assembly 100, including all of the sensors 110, 112, 114, 116, 118, is preferably located on a single printed circuit board 121.

Sensor data generated by the analog sensors 112, 114, 116 is typically a voltage signal proportional to the measured level of an air quality attribute. Analog sensor data is preferably converted to digital sensor data by analog-to-digital converter (A-to-D) 122 for use by the microprocessor 102. The digital sensors 110, 118 are directly coupled to the microprocessor 102. The microprocessor 102 converts raw sensor data to air quality data. The conversion to air quality data units is accomplished by custom software that references individual sensor specific calibration data. That is, test data that relates the sampled information, in this case analog to digital converter counts, to a known level of the parameter of interest.

The air quality data is then preferably converted by the microprocessor 102 to an appropriate communications protocol. Communications driver 124 transmits the air quality data to communications interface 132 and then to the private communications network 22 and/or an HVAC controller 134. In one embodiment, the communications interface 132 is compatible with a LAN protocol, such as Ethernet protocol. An HVAC controller is typically a programmable logic controller or other programmable device that controls the operation of various HVAC equipment. In another embodiment, the communications driver 124 transmits the air quality data directly to the HVAC controller 134. In yet another embodiment, the air quality data is transmitted through the private communications network 22 to the local HVAC controller 134. Since the communications driver 124 transmits digital data, the air quality data can be sent long distances with minimal interference from unwanted voltages or currents (i.e., noise).

Various sensors may be employed for measuring air velocity, dew point, air pressure, and/or the level of concentration of one or more undesirable gases in the ambient air, such as sulfur dioxide, methane, propane, and the like. Sensors that measure the level of particulates, such as dust, aerosol droplets, bacteria, spores, pollen, and viruses may also be used. For particulate detecting, an ionization detector or back scattering infra-red detector may be employed. An ionizing smoke or particle detector is commercially available from Dicon Safety Products, Inc. of Toronto, Ontario, Canada and can be adapted for use as a sensor by modifying the device to output a voltage proportional to the particles detected by the electrodes. Other sensors that produce an electronic signal proportional to the level of foreign substances present in the ambient air, such as toxins, molds, or other chemicals, may be employed and the invention is not intended to be limited to the particular sensors described. Suitable additional sensors are disclosed in U.S. Pat. No. 5,255,556 (Lobdell).

In one embodiment, the odor and gases sensor 114 provides a relative indication of air quality, without identifying particular VOC's present in the air. A broadband odor and gases sensor permits more cost-effective detection of VOC's. In one embodiment, the odor and gases sensor 114 is calibrated using a reference gas, such as toluene. For example, 0–100 ppm of toluene corresponds to 0–100% of the permitted level of VOC's. All VOC's detected by the sensor 114 are then combined and converted to a single indication of relative air quality on the scale of 0–100%.

Some of the sensors, such as the odor and gases sensor 114 and the CO sensor 116, typically need to be heated in order to operate accurately. Power regulator 128 provides current to resistance heaters in each of the sensors 116 and 118. The microprocessor 102 controls a digital potentiometer 130 that sets the proper level of heater operation. Additional circuitry then automatically re-adjusts the voltage supplied to the heater resistances of the odors and gasses, and CO sensors 114, 116 to continuously and accurately maintain the desired temperature. The desired temperature can be determined empirically or using data provided by the sensor manufacturer. Accurate control of the temperature prevents temperature changes from occurring and being interpreted as changes in the odor and gases or CO levels.

The present sensor assembly 100 offers a number of advantages over the prior art. By locating all of the sensors 110, 112, 114, 116, 118 in close proximity in a single assembly (or on a single printed circuit board), atmospheric separation is minimized between the sensors 110, 112, 114, 116, 118, and hence, provides increased accuracy over a plurality of discrete sensors. Minimizing atmospheric separation is particularly important when the output of one sensor is used to control, adjust and/or calibrate another sensor in the same sensor assembly 100. For example, carbon monoxide detection is affected by humidity. Microprocessor 102 is preferably programmed to adjust CO measurements for relative humidity measured by humidity sensor 112.

In one embodiment, a look-up table with error correction factors is stored in the memory circuit 104. The error correction factors are typically determined empirically for a given CO detector 116. The look-up table identifies the error in the CO sensor as a function of relative humidity. The microprocessor 102 receives input from the humidity sensor 112 and uses the look-up table to adjust the CO sensor data to reflect the relative humidity measured by sensor 112. In another embodiment, rather than a look-up table the microprocessor 102 runs an algorithm that determines the error correction for one sensor as a function of the input from another sensor on the same sensor assembly 100. For example, if the ambient temperature as measured by the temperature sensor 110 is above or below a threshold limit, the microprocessor 102 may adjust the input of one or more of the other sensors on the sensor assembly 100 to compensate for thermal expansion/contraction.

In another embodiment, the microprocessor 102 combines raw sensor data (e.g., voltages) and/or air quality data from two or more sensors to generate a composite air quality index. The present air quality index is a composite number that factors in the interdependency of various air quality attributes. For example, odors and gases are worse in the presence of higher humidity. A composite air quality index based upon the odors and gases sensor and the humidity sensor will more accurately reflect the true impact of the odors and gases than separate data for each of these sensors. Similarly, increased levels of $CO_2$ are more problematic at higher temperatures. Again, a composite air quality index that based upon data from the $CO_2$ and temperature sensors will more accurately reflect the impact of $CO_2$. In one embodiment, data from all of the sensors are combined into a single air quality index. In yet another embodiment, the controller 58 at the second private communications network 50 combines air quality data from two or more sensors to generate the air quality index.

In one embodiment, memory device 104 has sufficient capacity to store sensor data and/or air quality data for a discrete period of time. In the event that the communications link between a sensor assembly 40 and the second private communications network 50 fail, the sensor assembly 100 is capable of retaining the sensor data and/or air quality data for a period of time, such as for example seven days, until the connection is reestablished. Once the connection is reestablished, the microprocessor 102 downloads the stored air quality data to the private communications network 22 for processing as discussed herein.

In another embodiment, the microprocessor 102 is programmed to process and the memory device 104 is adapted to receive and store updated software from the private communications network 22. Any of the software stored in the memory device 104 can be updated, including without limitation the communications protocols, error correction tables, and the like. In this embodiment, the second private communications network 50 transmits software updates over the public communications network 30 through the gateway 32 to the private communications network 22. The private communications network 22 delivers the updated software to the sensor assembly 100 and the microprocessor 102 processes the updated software and stores it in the memory device 104. This feature permits a large number of sensor assemblies 100 to receive updated software from a remote private communications network 50 without requiring manual adjustment or on-site maintenance.

Figure 3:
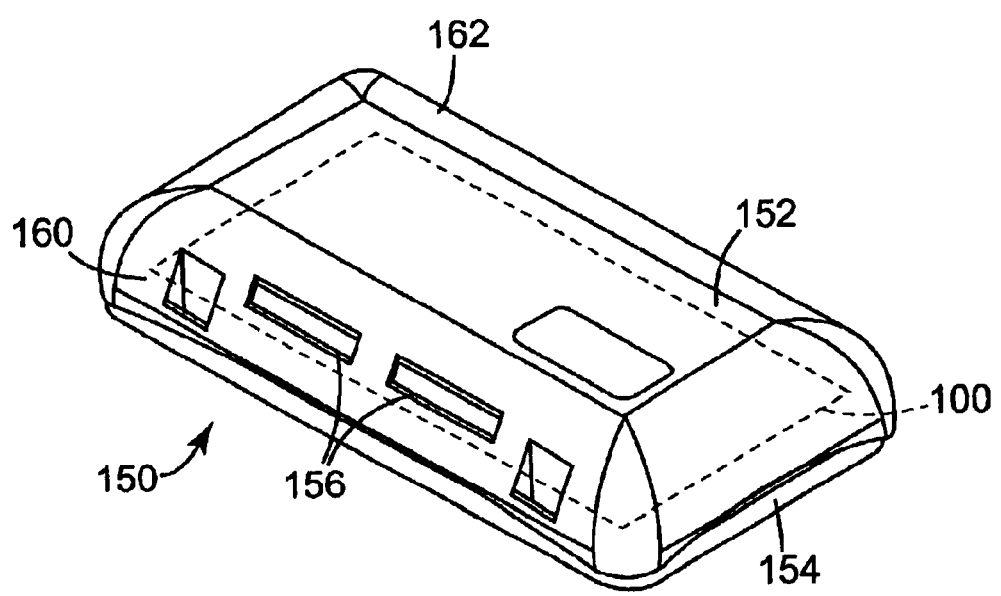
FIG. 3 is a perspective view of a housing for a sensor assembly in accordance with the present invention.

FIG. 3 is a perspective view of a housing 150 for the sensor assembly 100. The housing 150 includes a top portion 152 and a bottom portion 154. The top portion 152 includes a plurality of openings 156 to permit ambient air to flow reach the sensors 110, 112, 114, 116, 118 (see FIG. 2). In one embodiment, openings 156 are located along bottom edge 160 and top edge 162 of the top portion 152. Heat generated by some of the sensors, such as 114 and 116, creates a convection current that draws ambient air in at the bottom edge 160 and expels it out along the top edge 162. Thermal barrier 120 (see FIG. 2) prevents heat from the sensors 114, 116 from interfering with the operation of the other sensors, such as temperature sensor 110 and humidity sensor 112.

Suitable sensors are available from a number of manufactures. The specific sensors listed below are provided by way of example only.

Sample Temperature Sensor

A suitable temperature sensor 110 is available from Dallas Semiconductor under model number DS-18S20 high-precision, 1-wire digital thermometer. This device uses a single wire interface that requires only one port pin for communication and consumes zero standby power. As manufactured, the sensor measures temperatures from about −55° C. to +125° C. (−67° F. to +257° F.) with about a ±0.5° C. basic accuracy over the range of about −10° C. to +85° C.

The DS 18S20 has three main components: 1) 64-bit laser trimmed read only memory (ROM), 2) a high accuracy temperature sensor, 3) nonvolatile temperature alarm triggers for high and low temperature limits. The device derives its power from the 1-wire communication line by storing energy on an internal capacitor during periods of time when the signal line is high and continues to operate off this power source during the low times of the line until it returns high to replenish the parasitic (capacitor) supply. As an alternative, the DS18S20 may also be powered from about a 3 volt–5 volt supply.

The sensor includes analog circuitry to measure temperature and then converts the temperature signal to digital word and expresses it as a 9-bit digital value. An additional feature allows a software routine to be called from within the chip to produce a 12-bit digital value from the temperature signal for higher precision. Communication with the sensor is typically via a 1-wire port.

Sample Humidity Sensor

A suitable humidity sensor is available from Vaisala Oy (Helsinki, FI) under the trade designation HUMICAP® sensor and incorporates Vaisala's KTY85-110 relative humidity sensor. The HUMICAP® sensor was chosen because of its demonstrated repeatability, stability and performance in industrial control processes under very harsh conditions.

The basic principle of humidity measurement is based upon variable thin film capacitance. The thin polymer film either absorbs or exudes water vapor as the relative humidity of the ambient air rises or drops. The dielectric properties of the polymer film depend on the amount of water contained in it: as the relative humidity changes, the dielectric properties of the film change and so the capacitance of the sensor changes. The electronics of the instrument measure the capacitance of the sensor and convert it into a humidity reading. The HUMICAP® integrates signal-conditioning circuitry into a package along with the sensor chip itself.

Carbon Dioxide Sensor

A suitable carbon dioxide ($CO_2$) sensor is available from Tellaire. The module is a microprocessor driven device that emits and senses non-dispersive infrared radiation to determine $CO_2$ concentrations. The sensing system is executed through use of an application specific integrated circuit ("ASIC") that reads and processes the electrical signal produced by an optical source and detector built into a small, aluminum optical bench. The $CO_2$ module board is about 2×2.25×0.7 inches and communicates digitally with the central microprocessor of the sensor assembly.

The sensor uses a regulated 5 volt power supply and comes precalibrated by the manufacturer. Sensor software includes Tellaire's TEMA algorithm that can maintain calibration stability for approximately 5 years. The measurement range of the module is about 0–10,000 parts per million (ppm), with a resolution of about 1 ppm, Accuracy for typical conditions of about 60° to about 90° F. and about 760 millimeters of mercury (mm Hg) in the range of about 0 to about 2,000 ppm is ±50 ppm or about 3% of reading, whichever is greater. Accuracy for typical conditions over the range of about 2,000 to about 10,000 ppm is ±5% of the reading.

For extended operating conditions of about 32° to about 122° F. and about 760 mm Hg, 0–2,000 ppm accuracy is 1100 ppm or 5% of reading, whichever is greater, and for 2,000–10,000 ppm is ±7% of the reading. Repeatability is about +/−20 ppm. Pressure dependence is 0.13% of the reading per mm Hg. The annual drift is +/−20 ppm in typical conditions with a 5-year calibration interval.

The signal is updated about every 4 seconds. Warm up occurs in less than about 5 minutes. Operating conditions are about 0–50° C. with about 0–95% non-condensing relative humidity. The digital output is SPI/Microwire 1. Power consumption is about 135 milliamperes at peak use.

Sample Carbon Monoxide (CO) and Toluene Semiconductor Gas Sensor

Suitable CO and Gas/Odor Sensors (VOC's) are available from Capteur under model numbers NG107 CO sensor and AAL25 toluene sensor. These sensors use mixed-metal oxide semiconductor technology, which provides enhanced performance and sensor stability. Unlike tin-oxide sensors, the more advanced mixed-metal oxide sensors do not require catalysts or reagents to increase their sensitivity. Mixed-metal oxide sensors do not suffer from the noticeable aging typically associated with such reagents and catalysts, plus they are less susceptible to interference from relative humidity.

These solid-state gas sensors employ semiconducting oxides and are operated at temperatures above ambient. The electrical resistance of the sensor material depends upon the temperature, and also on the chemical composition of the surrounding atmosphere. Oxides change their resistance as the oxygen concentration in the atmosphere changes. Most of the semiconducting materials used in gas sensors share a common dependence of their resistance on the concentration of the target gas in the surrounding atmosphere. For most gases, except oxygen, the change in resistance per unit change in gas concentration is greatest at lower concentrations of the target gas, and it decreases as the concentration of the target gas increases. For these sensors the change in resistance varies as the square root of the concentration of the target gas.

The sensors are small, lightweight and provide long operational life, without the need for routine replacement. The sensors are expected to last at least 5 years, which is greater than other alternative technologies, such as electrochemical sensors. The sensors are made with ceramic fabrication processes that allow the microstructure of the sensors to be precisely controlled. Advanced thick film processing and an imbedded platinum heater allow for temperature compensation. Since the Capteur toluene sensor shows broad reactivity to TVOC, calibration of each sensor using NIST traceable concentrations of iso-butylene and an instrument with a traceable calibration set to respond to TVOC's is preferred.

Data Trending

Since the sensors 40 measure actual levels of air quality attributes, trends in air quality attributes can be tracked. For example, if a particular air quality attribute is changing linearly, the slope can be calculated and the time interval when the threshold limit values will be exceeded can be determined. In some embodiments, an alert can be sent indicating that a potential problem with air quality is anticipated.

Space Management System

Referring to FIG. 1, the present invention is also directed to using the private communications network 22 to provide a space management system 95 at the site 24. Space management entity 94 assumes responsibility for providing utility services 90, 92 sufficient to maintain certain air quality attributes within predetermined parameters at the site 24. The air quality monitoring system 20 records the performance of the space management entity 94 and provides real-time information about the environmental conditions at the site 24. As used herein, "space management system" refers to an arrangement where one provider is responsible for maintaining certain air quality attributes within predetermined parameters at a site.

In one embodiment, the site 24 contracts with the space management entity 94 to maintain the temperature and humidity at the site 24 within certain parameters. The price paid by the site 24 to the space management entity 94 can optionally vary depending on how closely the site 24 is maintained within the selected parameters. If humidity at the site 24 is outside the predetermined parameters, the price paid to the space management entity 94 can be automatically decreased The space management entity 94 is preferably responsible to contract with the utility providers 90, 92 as well as the provider of the air quality monitoring system 20. In the preferred embodiment, the site 24 receives a single invoice from the space management entity 94 rather than dealing with individual utilities and the air quality monitoring system provider. In another embodiment, the space management entity 94 is a utility provider.

All of the patents and patent applications disclosed herein, including those set forth in the Background of the Invention, are hereby incorporated by reference. Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

What we claimed is:

1. An air quality monitoring system at a site having a private communications network adapted to carry data traffic, the air quality monitoring system comprising:

at least one sensor assembly programmed to collect air quality data at the site, the sensor assembly comprising:
first and second air quality sensors adapted to measure a level of an air quality attribute, the first and second air quality sensors being coupled to a microprocessor and a data storage device;

a communications device coupling the microprocessor to the private communications network;

a public communications network coupled to the private communications network;

an archiving and processing system at a remote data collection site comprising a controller programmed to automatically acquire over the public communications network air quality data from one or more sensor assemblies and to automatically store air quality data in a database;

wherein the microprocessor is programmed to adjust sensor data from the first air quality sensor in response to sensor data collected by the second air quality sensor.

2. The system of claim 1 wherein each sensor assembly comprises a sensor assembly identification number.

3. The system of claim 1 wherein air quality data for a particular sensor comprises a format specific to the air quality attribute being measured.

4. The system of claim 1 wherein air quality data for a particular site is associated with a site identification number.

5. The system of claim 1 wherein the air quality sensor outputs a voltage signal proportional to a measured level of an air quality attribute.

6. The system of claim 1 wherein the microprocessor is programmed to convert sensor data to air quality data.

7. The system of claim 1 wherein the microprocessor is programmed to convert sensor data to an industrial control protocol.

8. The system of claim 1 wherein the microprocessor is programmed to convert sensor data to an industrial control protocol compatible with an HVAC controller.

9. The system of claim 1 wherein the microprocessor is coupled to an HVAC controller through the private communications network.

10. The system of claim 1 wherein the microprocessor is coupled directly to an HVAC controller.

11. The system of claim 1 wherein the microprocessor is programmed to systematically collect air quality data from the air quality sensors at defined intervals and to transmit the air quality data to the private communications network.

12. The system of claim 1 wherein the microprocessor is programmed to systematically collect air quality data from the air quality sensors at defined intervals and to transmit the air quality data over the private communications network and the public communications network to the archiving and processing system.

13. The system of claim 1 wherein the microprocessor is programmed to systematically collect air quality data from the air quality sensors at defined intervals and to store the air quality data in the data storage device.

14. The system of claim 1 wherein the data storage device comprises a read/write semiconductor memory device.

15. An air quality monitoring system at a site having a private communications network adapted to carry data traffic, the air quality monitoring system comprising:

at least one sensor assembly programmed to collect air quality data at the site, the sensor assembly comprising:

at least one air quality sensor adapted to measure a level of an air quality attribute, the air quality sensor being coupled to a microprocessor and a data storage device;

a communications device coupling the microprocessor to the private communication network;

a public communications network coupled to the private communications network;

an archiving and processing system at a remote data collection site comprising a controller programmed to automatically acquire over the public communications network air quality data from one or more sensor assemblies and to automatically store air quality data in a database;

wherein the archiving and processing system comprises a second private communications network coupled to the public communications network.

16. The system of claim 1 wherein the data storage device comprises sufficient storage capacity to store air quality data for about one week.

17. The system of claim 1 wherein the data storage device comprises an error correction table for one or more of the air quality sensors.

18. The system of claim 1 wherein the data storage device comprises a calibration table for one or more of the air quality sensors.

19. An air quality monitoring system at a site having a private communications network adapted to carry data traffic the air quality monitoring system comprising:

at least one sensor assembly programmed to collect air quality data at the site, the sensor assembly comprising:

at least one air quality sensor adapted to measure a level of an air quality attribute, the air quality sensor being coupled to a microprocessor and a data storage device;

a communications device coupling the microprocessor to the private communication network;

a public communications network coupled to the private communications network;

an archiving and processing system at a remote data collection site comprising a controller programmed to automatically acquire over the public communications network air quality data from one or more sensor assemblies and to automatically store air quality data in a database;

wherein the microprocessor is programmed to modify an error correction table for a first air quality sensor in response to sensor data from a second air quality sensor.

20. An air quality monitoring system at a site having a private communications network adapted to carry data traffic, the air quality monitoring system comprising:

at least one sensor assembly programmed to collect air quality data at the site, the sensor assembly comprising:

at least one air quality sensor adapted to measure a level of an air quality attribute, the air quality sensor being coupled to a microprocessor and a data storage device;

a communications device coupling the microprocessor to the private communication network;

a heater sensing and control circuit coupled to the microprocessor; and a heater controlled by the heater sensing and control circuit operatively coupled to one or more temperature dependent sensors a public communications network coupled to the private communications network;

an archiving and processing system at a remote data collection site comprising a controller programmed to automatically acquire over the public communications network air quality data from one or more sensor assemblies and to automatically store air quality data in a database.

21. The system of claim 20 wherein the microprocessor is programmed to calibrate one or more of the temperature dependent sensors.

22. An air quality monitoring system at a site having a private communications network adapted to carry data traffic, the air quality monitoring system comprising:
at least one sensor assembly programmed to collect air quality data at the site, the sensor assembly comprising:
at least one air quality sensor adapted to measure a level of an air quality attribute, the air quality sensor being coupled to a microprocessor and a data storage device;
a communications device coupling the microprocessor to the private communication network;
a public communications network coupled to the private communications network;
an archiving and processing system at a remote data collection site comprising a controller programmed to automatically acquire over the public communications network air quality data from one or more sensor assemblies and to automatically store air quality data in a database;
wherein the microprocessor is programmed to adjust one or more heaters adjacent to one or more temperature dependent sensors to maintain an operating temperature within a specified tolerance.

23. The system of claim 1 wherein the communications device is programmed to transmit digital data corresponding to the air quality data to the private communications network.

24. The system of claim 1 comprising a communications interface programmed to convert air quality data transmitted by the communications device to a protocol compatible with the private communications network.

25. The system of claim 24 wherein the air quality sensor is adapted to generate sensor data and the microprocessor is programmed to convert the sensor data into a protocol compatible with the communications interface.

26. The system of claim 1 wherein the air quality sensor is adapted to generate sensor data and the microprocessor is programmed to convert the sensor data into a communications protocol compatible with the private communications network.

27. The system of claim 1 comprising a remote site coupled to the database through the public communications network.

28. The system of claim 1 wherein a plurality of the sensor assemblies are located at distributed locations throughout the site.

29. The system of claim 1 wherein private communications network is coupled to the public communications network over a dedicated communications line.

30. The system of claim 15 wherein the second private communications network is coupled to the public communications network over a dedicated communications line.

31. The system of claim 30 comprising a gateway through which the second private communications network communicates with the public communications network.

32. The system of claim 1 comprising a gateway through which the private communications network communicates with the public communications network.

33. The system of claim 32 wherein the communications device couples the microprocessor with the private communications network downstream of the gateway.

34. The system of claim 1 wherein the archiving and processing system is programmed to store air quality data at discrete time intervals and calculate an average.

35. An air quality monitoring system at a site having a private communications network adapted to carry data traffic, the air quality monitoring system comprising:
at least one sensor assembly programmed to collect air quality data at the site, the sensor assembly comprising:
at least one air quality sensor adapted to measure a level of an air quality attribute, the air quality sensor being coupled to a microprocessor and a data storage device;
a communications device coupling the microprocessor to the private communication network;
a public communications network coupled to the private communications network;
an archiving and processing system at a remote data collection site comprising a controller programmed to automatically acquire over the public communications network air quality data from one or more sensor assemblies and to automatically store air quality data in a database;
wherein the archiving and processing system comprises a first archiving and processing system at a first remote data collection site and a second archiving and processing system at a second remote data collection site.

36. The system of claim 35 comprising a synchronizing connection between first and second archiving and processing systems.

37. The system of claim 1 wherein the archiving and processing system is programmed to send an alert signal when air quality data is outside defined operating parameters.

38. The system of claim 37 wherein the archiving and processing system is programmed to send an alert over the public communications network to the private communications network or a remote site.

39. The system of claim 37 wherein the alert comprises one or more of an e-mail message, an automated telephone message, an automated fax, or an automated pager message.

40. The system of claim 1 wherein the controller is programmed to calculate trends in air quality data.

41. The system of claim 1 wherein the archiving and processing system is programmed to send an alert signal when a calculated trend predicts that air quality data will be outside defined operating parameters within a defined time interval.

42. The system of claim 1 wherein the microprocessor is adapted to combine air quality data from two or more air quality sensors to provide an air quality index.

43. The system of claim 1 wherein the archiving and processing system is adapted to combine air quality data from two or more air quality sensors to provide an air quality index.

44. The system of claim 1 wherein the sensor is adapted to provide a relative indication of air quality based upon the presence of a plurality of VOC's.

45. An air quality monitoring system comprising:
a site having a private communications network adapted to carry data traffic;
at least one sensor assembly programmed to collect air quality data at the site, the sensor assembly comprising:
first and second air quality sensors adapted to measure a level of an air quality attribute, the first and second air quality sensors coupled to a microprocessor and a data storage device;
a communications device coupling the microprocessor to the private communications network;
a public communications network coupled to the private communications network;
an archiving and processing system at a remote data collection site comprising a controller programmed to automatically acquire over the public communications network air quality data from one or more of the sensor assemblies and to store air quality data from the sensor assemblies in a database;

wherein the microprocessor is programmed to adjust sensor data from the first air quality sensor in response to sensor data collected by the second air quality sensor.

46. An air quality monitoring system comprising:
a site having a private communications network adapted to carry data traffic;
at least one sensor assembly programmed to collect air quality data at the site, the sensor assembly comprising:
at least one air quality sensor adapted to measure a level of an air quality attribute, the air quality sensor coupled to a microprocessor and a data storage device;
a communications device coupling the microprocessor to the private communications network;
a public communications network coupled to the private communications network;
an archiving and processing system at a remote data collection site comprising a controller programmed to automatically acquire over the public communication network air quality data from one or more of the sensor assemblies and to store air quality data from the sensor assemblies in a database;
wherein the archiving and processing system comprises a second private communications network coupled to the public communications network.

47. An air quality monitoring system at a site having a private communications network adapted to carry data traffic, the air quality monitoring system comprising:
at least one sensor assembly programmed to collect air quality data at the site, the sensor assembly comprising:
first and second air quality sensors adapted to measure a level of an air quality attribute, the air quality sensor coupled to a microprocessor and a data storage device;
a communications device coupling the microprocessor to the private communications network;
an archiving and processing system coupled to the private communications network and located at the site but remote from the sensor assemblies comprising a controller programmed to automatically store air quality data from the sensor assemblies in a database;
wherein the microprocessor is programmed to adjust sensor data from the first air quality sensor in response to sensor data collected by the second air quality sensor.

48. The system of claim 47 wherein the private communications network is coupled to a public communications network.

49. An air quality monitoring system comprising:
a site having a private communications network adapted to carry data traffic;
at least one sensor assembly programmed to collect air quality data at the site, the sensor assembly comprising:
at least one air quality sensor adapted to measure a level of an air quality attribute, the air quality sensor coupled to a microprocessor and a data storage device;
a communications device coupling the microprocessor to the private communications network;
an archiving and processing system coupled to the private communications network and located at the site but remote from the air quality sensor comprising a controller programmed to automatically store air quality data from the sensor assemblies in a database.

50. The system of claim 49 wherein the private communications network is coupled to a public communications network.

51. A method for monitoring air quality comprising the steps of:
coupling one or more sensor assemblies programmed to collect air quality data to a private communications network located at a site;
measuring the level of one or more air quality attributes using air quality sensors in the sensor assemblies;
converting sensor data to air quality data;
uploading the air quality data to the private communications network;
transmitting the air quality data over a public communications network to a second private communications network;
automatically storing the air quality data from one or more sensor assemblies in a database on the second private communications network; and
providing access to the air quality data in the database through the public communications network.

52. The method of claim 51 comprising the step of measuring a plurality of air quality attributes at each sensor assembly.

53. The method of claim 51 comprising the step of identifying each air quality sensor with a sensor identification number or schema.

54. The method of claim 51 comprising the step of identifying each sensor assembly with a sensor assembly identification number.

55. The method of claim 51 comprising the step of identifying each site with a site identification number.

56. The method of claim 51 comprising the step of converting sensor data to an industrial control protocol.

57. The method of claim 51 comprising the step of collecting air quality data from the air quality sensors at defined intervals and transmitting the air quality data to the private Communications network.

58. The method of claim 51 comprising the step of transmitting the air quality data over the private communications network and the public communications network to the archiving and processing system at defined intervals.

59. The method of claim 51 comprising the step of temporarily storing the air quality data in a data storage device in the sensor assembly.

60. The method of claim 51 comprising the step of adjusting sensor data from one or more of the air quality sensors using an error correction table.

61. The method of claim 51 comprising the step of calibrating one or more of the air quality sensors using a calibration table retained in the sensor assembly.

62. The method of claim 51 comprising the step of adjusting sensor data from a first air quality sensor in response to sensor data collected by a second air quality sensor.

63. The method of claim 51 comprising the step of modifying an error correction table for a first air quality sensor in response to sensor data from a second air quality sensor.

64. The method of claim 51 comprising the step of heating one or more of the sensors to an operating temperature.

65. The method of claim 51 comprising the step of converting air quality data at a communications interface to a protocol compatible with the private communications network.

66. The method of claim 51 comprising the step of converting air quality data at the sensor assembly to a protocol compatible with the private communications network.

67. The method of claim 51 comprising the step of converting air quality data to a protocol compatible with an HVAC controller.

68. The method of claim 51 comprising the step of storing air quality sensor data at discrete time intervals as an average of multiple readings.

69. The method of claim 51 comprising the step of transmitting an alert from the second private communications network over the public communications network when air quality data is outside defined operating parameters.

70. The method of claim 69 wherein the alert comprises one or more of an e-mail message, an automated telephone message, or an automated pager message.

71. The method of claim 51 comprising the step of calculating trends in the air quality data.

72. The method of claim 51 comprising the step of sending an alert signal from the second private communications network over the public communications network when a calculated trend in air quality data is predicted to be outside defined operating parameters within a defined time interval.

73. A sensor assembly for use at a site having a private communications network that is adapted to carry data traffic, the sensor assembly comprising:
   first and second air quality sensors adapted to measure a level of an air quality attribute;
   a microprocessor coupled to the air quality sensor and to a data storage device, the microprocessor programmed to convert sensor data to a protocol compatible with the private communications network; and
   a communications device coupling the microprocessor to the private communications network;
   wherein the microprocessor is programmed to adjust sensor data from the first air quality sensor in response to sensor data collected by the second air quality sensor.

74. The apparatus of claim 73 wherein each sensor assembly comprises a sensor assembly identification number.

75. The apparatus of claim 73 wherein air quality data for a particular sensor comprises a format specific to the air quality attribute being measured.

76. The apparatus of claim 73 wherein the microprocessor is adapted to combine air quality data from two or more air quality sensors to provide an air quality index.

77. The apparatus of claim 73 wherein the archiving and processing system is adapted to combine air quality data from two or more air quality sensors to provide an air quality index.

78. The apparatus of claim 73 wherein the air quality sensor is adapted to provide a relative indication of air quality based upon the presence of a plurality of VOC's.

79. The apparatus of claim 73 wherein the microprocessor is programmed to convert sensor data to an industrial control protocol.

80. The apparatus of claim 73 wherein the microprocessor is programmed to systematically collect air quality data from the air quality sensors at defined intervals and to transmit the air quality data to the private communications network.

81. The apparatus of claim 73 wherein the microprocessor is programmed to systematically collect air quality data from the air quality sensors at defined intervals and to transmit the air quality data over the private communications network and a public communications network to an archiving and processing system.

82. The apparatus of claim 73 wherein the microprocessor is programmed to systematically collect air quality data from the air quality sensors at defined intervals and to store the air quality data in the data storage device.

83. The apparatus of claim 73 wherein the data storage device comprises sufficient storage capacity to store air quality data for a period of time.

84. The apparatus of claim 73 wherein the data storage device comprises an error correction table for one or more of the air quality sensors.

85. The apparatus of claim 73 wherein the data storage device comprises a calibration table for one or more of the air quality sensors.

86. A sensor assembly for use at a site having a private communications network that is adapted to carry data traffic, the sensor assembly comprising:
   at least one air quality sensor adapted to measure a level of an air quality attribute;
   a microprocessor coupled to the air quality sensor and to a data storage device, the microprocessor programmed to convert sensor data to a protocol compatible with the private communications network; and
   a communications device coupling the microprocessor to the private communications network;
   wherein the microprocessor is programmed to modify an error correction table for a first air quality sensor in response to sensor data from a second air quality sensor.

87. A sensor assembly for use at a site having a private communications network that is adapted to carry data traffic, the sensor assembly comprising:
   at least one air quality sensor adapted to measure a level of an air quality attribute;
   a microprocessor coupled to the air quality sensor and to a data storage device, the microprocessor programmed to convert sensor data to a protocol compatible with the private communications network;
   a communications device coupling the microprocessor to the private communications network;
   a heater sensing and control circuit coupled to the microprocessor; and
   a heater controlled by the heater sensing and control circuit operatively coupled to one or more temperature dependent sensors.

88. The apparatus of claim 87 wherein the microprocessor is programmed to adjust one or more of the temperature dependent sensors to an operating temperature.

89. The apparatus of claim 73 comprising a communications interface programmed to convert air quality data transmitted by the communications device to a protocol compatible with the private communications network.

90. A sensor assembly for use at a site having an HVAC controller that is adapted to control HVAC equipment in response to environmental conditions, the sensor assembly comprising:
   at least a first air quality sensor and a second air quality sensor each adapted to measure a level of at least one air quality attribute;
   a microprocessor coupled to the air quality sensors and to a data storage device, the microprocessor programmed to convert sensor data to a protocol compatible with the HVAC controller and to adjust sensor data from the first air quality sensor in response to sensor data collected by the second air quality sensor, and
   a communications device coupling the microprocessor to the HVAC controller.

91. The assembly of claim 90 wherein the data storage device comprises an error correction table for one or more of the air quality sensors.

92. The assembly of claim 90 wherein the data storage device comprises a calibration table for one or more of the air quality sensors.

93. The assembly of claim 90 wherein the microprocessor is programmed to modify an error correction table for the first air quality sensor in response to sensor data from the second air quality sensor.

94. The assembly of claim 90 wherein the microprocessor is programmed to run an error correction algorithm for the first air quality sensor in response to sensor data from the second air quality sensor.

95. The assembly of claim 90 comprising:
- a beater sensing and control circuit coupled to the microprocessor, and
- a heater controlled by the heater sensing and control circuit operatively coupled to one or more temperature dependent sensors.

96. The assembly of claim 95 wherein the microprocessor is programmed to calibrate one or more of the temperature dependent sensors.

97. The assembly of claim 90 wherein the microprocessor is programmed to adjust one or more heaters adjacent to one or more temperature dependent sensors to maintain an operating temperature within a specified tolerance.

98. The assembly of claim 90 wherein the microprocessor is programmed to modify air quality data from the first air quality sensor in response to temperature data from the second air quality sensor.

99. The assembly of claim 98 wherein the air quality data from the first air quality sensor is modified in response to temperature data above or below a temperature threshold.

100. The assembly of claim 90 wherein the microprocessor is coupled to the HVAC controller through a private communications network.

* * * * *

UNITED STATES PATENT AND TRADEMARK OFFICE
CERTIFICATE OF CORRECTION

PATENT NO.  : 6,782,351 B2
DATED       : August 24, 2004
INVENTOR(S) : Bryan S. Reichel et al.

It is certified that error appears in the above-identified patent and that said Letters Patent is hereby corrected as shown below:

Column 23,
Line 16, "beater" should be changed to -- heater --.

Signed and Sealed this

Eighth Day of February, 2005

JON W. DUDAS
*Director of the United States Patent and Trademark Office*